United States Patent
Manzer et al.

(10) Patent No.: US 7,348,442 B2
(45) Date of Patent: Mar. 25, 2008

(54) GAS PHASE SYNTHESIS OF METHYLENE LACTONES USING CATALYSTS DERIVED FROM HYDROTALCITE PRECURSORS

(75) Inventors: Leo Ernest Manzer, Wilmington, DE (US); Kostantinos Kourtakis, Media, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 361 days.

(21) Appl. No.: 11/252,273

(22) Filed: Oct. 17, 2005

(65) Prior Publication Data

US 2006/0084818 A1   Apr. 20, 2006

Related U.S. Application Data

(60) Provisional application No. 60/619,730, filed on Oct. 18, 2004.

(51) Int. Cl.
*C07D 307/20* (2006.01)

(52) U.S. Cl. ............................................... 549/326
(58) Field of Classification Search ................ 549/326
See application file for complete search history.

(56) References Cited

U.S. PATENT DOCUMENTS 6,313,318 B1   11/2001   Coulson et al.

FOREIGN PATENT DOCUMENTS

WO   WO 99/52628   10/1999

OTHER PUBLICATIONS

V. K. Diez et al., Latin American Applied Research, 33, 79-86 (2003).
N. N. Das et al, Bull. Mater. Sci. 25, (4) 283-289 (2002).

*Primary Examiner*—Taofiq Solola

(57) ABSTRACT

Process for converting certain lactones to their alpha-methylene substituted forms using (i) a catalyst derived from a hydrotalcite or (ii) a composite catalyst comprising the hydrotalcite-derived catalyst into which at least one of lithium, sodium, potassium, rubidium, cesium, magnesium, calcium, strontium, barium has been incorporated.

3 Claims, 2 Drawing Sheets

GAS PHASE SYNTHESIS OF METHYLENE LACTONES USING CATALYSTS DERIVED FROM HYDROTALCITE PRECURSORS

CROSS-REFERENCE TO RELATED APPLICATION

This application claims priority under 35 U.S.C. §119 from U.S. Provisional Application Ser. No. 60/619,730 filed Oct. 18, 2004.

FIELD OF INVENTION

The invention pertains to a method of producing unsubstituted and substituted alpha-methylene lactones by a gas phase reaction of starting lactones with formaldehyde in the presence of a catalyst derived from a hydrotalcite.

BACKGROUND

Alpha-methylene-gamma-butyrolactone and methyl alpha-methylene-gamma-butyrolactone are useful monomers in the preparation of both homopolymers and copolymers. In addition, the alpha-methylene-gamma-butyrolactone group is an important structural feature of many sesquiterpenes of biological importance.

U.S. Pat. No. 6,313,318 describes a method for converting certain starting lactones to alpha-methylene substituted lactones using a so-called basic catalyst that is made by treating silica with an inorganic salt of Ba, Mg, K, Cd, Rb, Na, Li, Sr, and La. A problem with silica-based catalysts is that they are hydrothermally unstable under reaction conditions involving temperatures above about 250° C. In addition, regeneration cycles involving air produce water at high temperature, and the water can change the porosity and activity of the catalyst.

The prior art in this area involves the use of supported catalysts on silica, which are known to be hydrothermally unstable (see for instance, WO9952628A1). Under reaction conditions, or after repeated regeneration cycles, a hydrothermally unstable material will show catalytic performance that will deteriorate with time.

Hydrotalcites are layered, double hydroxides of general formula $$(M^{2+}_{1-x}M^{3+}_x(OH)_2)(A^{n-}_{x/n}) \cdot yH_2O$$

wherein the $M^{2+}$ ions can be a variety of divalent cations (e.g., Mg, Ni, Zn, Co, Fe, Cu) and the $M^{3+}$ ions can be Al, Fe or Cr. Some hydrotalcites are described by V. K. Diez, C. R. Apesteguia, and J. I. DiCosimo (*Latin American Applied Research*, 33, 79-86 (2003)) and N. N. Das and S. C. Srivastava (*Bull. Mater. Sci.* 25, (4), 283-289 (2002)).

Although hydrotalcites are known, and the thermal decomposition of them is known to produce materials that are catalytic for some purposes, their thermal decomposition to produce catalysts for lactone methylenation has not been described. The catalytic activity of such materials for lactone conversion reactions cannot be predicted because of the unpredictable nature of catalysis in general.

It would be advantageous, however, to have a lactone methylenation catalyst that is hydrothermally stable at high temperatures and whose activity does not decay with time on stream (TOS) or after several high temperature oxidizing regenerations.

SUMMARY OF THE INVENTION

This invention is based on the discovery that catalysts derived from hydrotalcites (as described below) and composites thereof (as defined below) are surprisingly active for lactone methylenation, with the advantage that they should possess superior hydrothermal stability compared to prior art supported silica catalysts.

In its first aspect, the present invention is a process for preparing a reaction product comprising an alpha-methylene lactone of the Formula II, said process comprising reacting a lactone of the Formula I with formaldehyde,

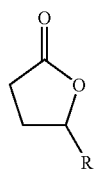

I

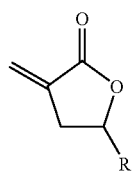

II wherein R is selected from the group consisting of hydrogen, methyl, ethyl, and straight or branched $C_3$-$C_5$ alkyl;

at a temperature in the range of from about 150° C. to about 450° C. in the presence of a catalyst derived from a hydrotalcite of the formula:

$$(M^{2+}_{1-x}M^{3+}_x(OH)_2)(A^{n-}_{x/n}) \cdot yH_2O$$

wherein $M^{2+}$ is Mg, or a combination of Mg and at least one of Zn, Ni, Co, Fe, and Cu; and $M^{3+}$ is Al, or a combination of Al and at least one of Fe and Cr; x is 0.66 to 0.1 and A is $CO_3$ with n=2 or OH with n=1, by a process comprising heating the hydrotalcite for a time and a temperature sufficient to cause a diminution in the hydrotalcite powder X-ray diffraction pattern peak intensities between 2θ angles of 10 degrees and 70 degrees using $CuK_\alpha$ radiation. Up to about one third of the Mg may be substituted with at least one of Zn, Ni, Co Fe and Cu, and up to about one third of the Al may be substituted with at least one of Fe and Cr. In a preferred embodiment of this invention, $M^{2+}$ is Mg, $M^{3+}$ is Al and $A^{n-}=CO_3^{2-}$.

In a highly preferred embodiment, the hydrotalcite is one in which $M^{2+}$=Zn and Mg combination, $M^{3+}$=Al, and x=0.382 with atomic ratios of Zn 0.16 Mg 0.46 Al 0.382.

More specifically, the hydrotalcite-derived catalyst is made by a process comprising:
(a) combining at least one aluminum salt and at least one magnesium salt, and optionally at least one salt of an element selected from the group consisting of Zn, Ni, Co, Fe, Cu and Cr, to form an aqueous solution;
(b) optionally heating the aqueous solution to 60° C.;
(c) adjusting the pH of the material produced in step (a) or step (b) with base or sodium carbonate to precipitate any hydroxides, carbonates, or hydroxide carbonates that are formed;
(d) drying the material produced in step (c) to produce a hydrotalcite; and
(e) heating the hydrotalcite produced in step (d) for a time and a temperature sufficient to cause a diminution in the hydrotalcite powder X-ray diffraction pattern peak intensities between 2θ angles of 10 degrees and 70 degrees using $CuK_\alpha$ radiation.

In its second aspect, the invention involves the same lactone reaction wherein the catalyst is a composite catalyst that is made by a process comprising:

(f) contacting (i) the product produced in step (e) with (ii) a solution comprising a solvent and a compound of at least one element selected from the group consisting of lithium, sodium, potassium, rubidium, cesium, magnesium, calcium, strontium and barium;

(g) drying the product of step (f) to remove at least a portion of the solvent;

(h) heating the product of step (g) at a temperature in the range of 350° C. to 550° C. to produce a catalyst precursor; and (i) flushing at a preselected flow rate an oxygen-containing gas over said catalyst precursor either during step (h), or after step (h) while the temperature is still in the range of 350° C. to 550° C. to produce the composite catalyst in which the at least one element is present in said composite catalyst in an amount from about 0.1% to about 40% by weight of the combined weight of the product produced in step (e) and the element.

Catalysts used in the present invention might be expected to confer a hydrothermal stability advantage over silica-based catalysts on the theory that any enhancement of the lattice energy of a solid will yield a thermally and hydrothermally stable material. In terms of their fundamental inorganic properties, magnesium and aluminum are more ionic compared to the silicon oxides by virtue of the strongly cationic magnesium, and, to a lesser extent, aluminum cation compared to silicon. Theory suggests that this should, in turn, strengthen the interactions between the positively and negatively charged species in the lattice, stabilizing the structure.

BRIEF DESCRIPTION OF THE DRAWING

The Drawing consists of two figures.

DETAILED DESCRIPTION OF THE INVENTION

Figure 1:
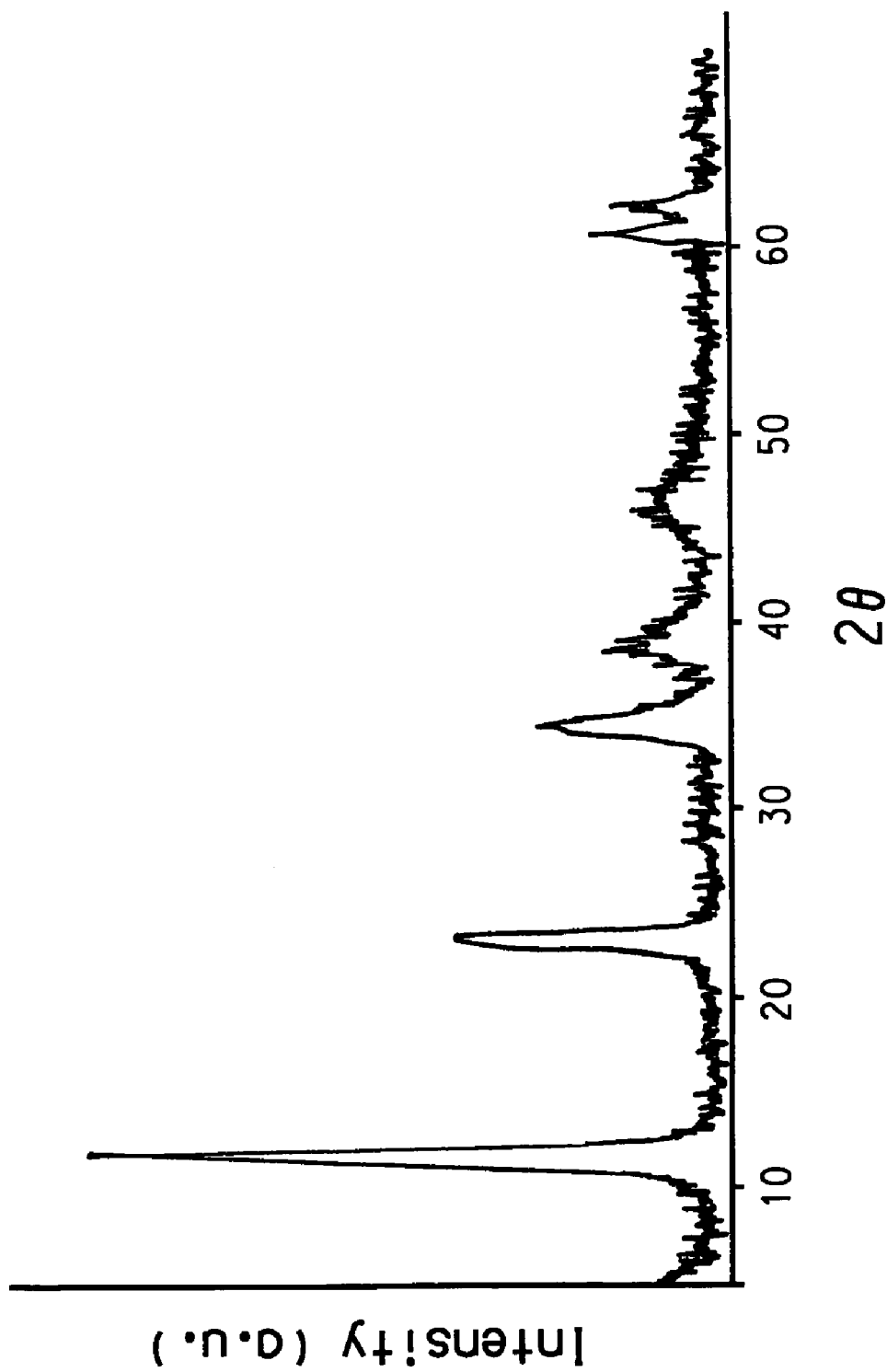
FIG. 1 is a powder X-ray diffraction pattern of a typical hydrotaclcite.

The following terms generally are abbreviated as follows:

alpha-methylene-gamma-butyrolactone is abbreviated MBL;

gamma-butyrolactone is abbreviated GBL;

gamma-valerolactone is abbreviated GVL;

alpha-methylene-gamma-valerolactone is abbreviated MVL;

gamma-methyl alpha methylene gamma butyrolactone is abbreviated MeMBL;

gas chromatography is abbreviated GC;

mass spectroscopy is abbreviated MS;

time on stream is sometimes abbreviated TOS; and standard cubic centimeters in abbreviated sccm.

The process of the present invention concerns a gas phase methylenation of lactones of Formula I to yield alpha-methylene lactones of Formula II.

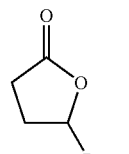

I

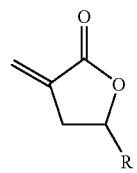

II

Specifically, lactone of Formula I is reacted with formaldehyde to give a reaction product comprising alpha methylene lactones of Formula II. The substituent —R group is selected from the group consisting of hydrogen, methyl, ethyl, and straight or branched $C_3$-$C_5$ alkyl.

In a preferred embodiment, the lactone of Formula I is gamma-butyrolactone (R is H) and the alpha-methylene lactone of Formula II is alpha-methylene-gamma-butyrolactone. In another preferred embodiment, the lactone of Formula I is methyl gamma-butyrolactone (R is methyl) and the alpha-methylene lactone of Formula II is gamma-methyl alpha-methylene gamma-butyrolactone.

The process of the present invention is carried out in the gas phase, at a temperature in the range of from about 150° C. to about 450° C. A temperature in the range of from about 250° C. to about 400° C. is preferred. A temperature in the range of from about 300° C. to about 340° C. is most preferred.

The reaction can be carried out at pressures ranging from about 0.1 MPa to about 1.0 MPa, with a preferred range of from about 0.1 MPa to about 0.5 MPa. Contact time with the catalyst can be selected to achieve desired yields and selectivities. Contact time can be manipulated by increasing or decreasing flow rates over the catalyst.

The formaldehyde may be supplied to the reaction in the form of an aqueous solution (formalin), a hemiacetal of an alcohol, a low molecular weight polyformaldehyde or formaldehyde trimer (trioxane). Formalin is preferred, because it is the lowest cost source of formaldehyde. The use of the trimers and oligomers, however, reduces the need to remove water from the process. Anhydrous formaldehyde can also be used. Hemiacetals work effectively, but require separate steps to release the formaldehyde from the alcohol and to recover and recycle the alcohol.

The catalyst used in the present invention is made from a hydrotalcite having the formula:

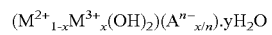

wherein $M^{2+}$ is Mg, or a combination of Mg and at least one of Zn, Ni, Co, Fe, and Cu; and $M^{3+}$ is Al, or a combination of Al and at least one of Fe and Cr; x is 0.66 to 0.1 and A is $CO_3$ with n=2 or OH with n=1.

The catalyst can be made by a process (is obtainable by a process) that comprises heating the hydrotalcite for a time and a temperature sufficient to cause a diminution in the hydrotalcite powder X-ray diffraction pattern peak intensities between 2θ angles of 10 degrees and 70 degrees using $CuK_\alpha$ radiation.

More specifically, the hydrotalcite-derived catalyst is made by a process comprising:

(a) combining at least one aluminum salt and at least one magnesium salt, and optionally at least one salt of an element selected from the group consisting of Zn, Ni, Co, Fe, Cu and Cr, to form an aqueous solution;

(b) optionally heating the aqueous solution to 60° C.;

(c) adjusting the pH of the material produced in step (a) or step (b) with base or sodium carbonate to precipitate any hydroxides, carbonates, or hydroxide carbonates that are formed;

(d) drying the material produced in step (c) to produce a hydrotalcite; and (e) heating the hydrotalcite produced in step (d) for a time and a temperature sufficient to cause a diminution in the hydrotalcite powder X-ray diffraction pattern peak intensities between 2θ angles of 10 degrees and 70 degrees using $CuK_\alpha$ radiation.

The salts may be any water-soluble salt including, without limitation nitrates, acetates, acetylacetonates, chlorides, and sulfates.

The starting hydrotalcite materials can be characterized by their powder X-ray diffraction characteristics. For example, powder x-ray diffraction data can be obtained with a PANALYTICAL X'PERT automated powder diffractometer, Model 3040. Samples are run in a batch mode using a Model PW3065 or PW1775 multi-position sample changer. The diffractometer is equipped with an automatic variable slits, a zenon proportional counter, and a graphit monochromator. The radiation can be CuK(ALPHA) (45 kV, 40 mA). Data are typically collected at room temperature from 2 to 90 deg. 2-theta; a continuous scan with an equivalent step size of 0.03 deg; and a count time of 2.0 sec. per step. If another alternative radiation is used (e.g. CoKα) the diffraction angles can be recomputed to the radiation of Cu wavelength by using the relation $2d \sin \theta = n\lambda$, where λ=the wavelength of the X-ray radiation, and θ is ½ of the 2θ value which is typically tabulated in the XRD diffraction patterns.

The diffraction pattern of a hydrotalcite is typically indexed on a rhombohedral or hexagonal unit cell. It is typically a layered structure. Typical diffraction lines have reflections at 11.28 degrees 2θ, 22.78, degrees 2θ, and 34.46 degrees 2θ, which correspond to the crystal composition $Mg_6 Al_2 (OH)_{16} CO_3 \cdot 4H_2O$ (Ross, G.; Kodama, H., Am. Mireal., 52 1036 (1967). This corresponds to x=0.333, n=2, $A=CO_3$, y=4, $M^{2+}=Mg$, $M^{3+}=Al$ in the formula:

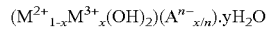

Other hydrotalcite compositions exhibit very similar diffraction patterns. However, the position of the peaks will shift slightly depending on the crystallographic unit cell of the other hydrotalcites. Hence, in FIG. 1 (taken from N. N. Das, S. C. Srivastava, Bull. Mater. Sci., Vol 25, no. 4, 283-289 (2002)), an essentially similar pattern will be obtained, but with a slight shift in the 2θ positions of the first three intense peaks.

$Mg_6 Al_2 (OH)_{18} \cdot 4.5H_2O$ (Mascolo, M. Mineral. Mag., 43 619 (1980), corresponding to x=0.333, n=1, A=OH, y=4.5, $M^{2+}=Mg$, $M^{3+}=Al$ in the formula:

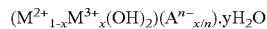

shows diffraction peaks at 11.335, 22.841, and 34.742 degrees 2θ, in essentially the same pattern, which characterizes this phase with slightly changed diffraction angles.

Precipitation of the aqueous solution of magnesium or aluminum salts, preferably nitrates, can be accomplished using sodium hydroxide or sodium carbonate. In the former case, if care is given to ensure the absence of contact of the material with $CO_2$, the pure hydroxide hydrotalcite phase is formed. In the case of reaction with sodium carbonate, a carbonate-containing hydrotalcite phase is formed.

The starting hydrotalcite may be thermally decomposed using conditions (time, temperature and atmosphere) to accomplish the diminution of the intensity of the powder X-ray diffraction peaks characteristic of the hydrotalcite phase.

Heating can be accomplished in air or in a combination of an inert gas such as nitrogen, argon, krypton for parts of the cycle. If a carbonate-free hydrotaclite is desired (A=OH⁻), heating must be accomplished in the absence of $CO_2$ or $CO_2$ generating reagents. In that case, an inert atmosphere is desired for all heating steps.

The hydrotalcite can be optionally dried at 120° C. in nitrogen, another inert gas or air (air in the case of carbonate containing hydrotalcites, or $A=CO_3^{2-}$) for a period of 30 minutes to 2 hours. Following the drying step, the hydrotaclite can be heated in air (for $A=CO_3^{2-}$) or nitrogen to a temperature of approximately 350 to 550° C. for a period of approximately 30 minutes to 48 hours. A heating rate of about 5° C./minute is preferred. The exact choice of temperature and heating time at temperature, or the number of these heating cycles, will depend on the hydrotalcite composition and its thermal stability. The conditions needed for any given composition can be chosen based on an examination of the powder X-ray diffraction patterns of the heated materials. The extent of the decomposition of the hydrotalcite can be determined by examining the diminution of the intensities of the first three X-ray diffraction peaks of the hydrotalcite phase as shown in FIG. 1. Typically, greater than 30% reduction in the X-ray diffraction peak intensity means that a portion of the hydrotalcite has decomposed, and this material, which now contains a decomposed hydrotalcite material, is within the scope of this invention.

Figure 2:
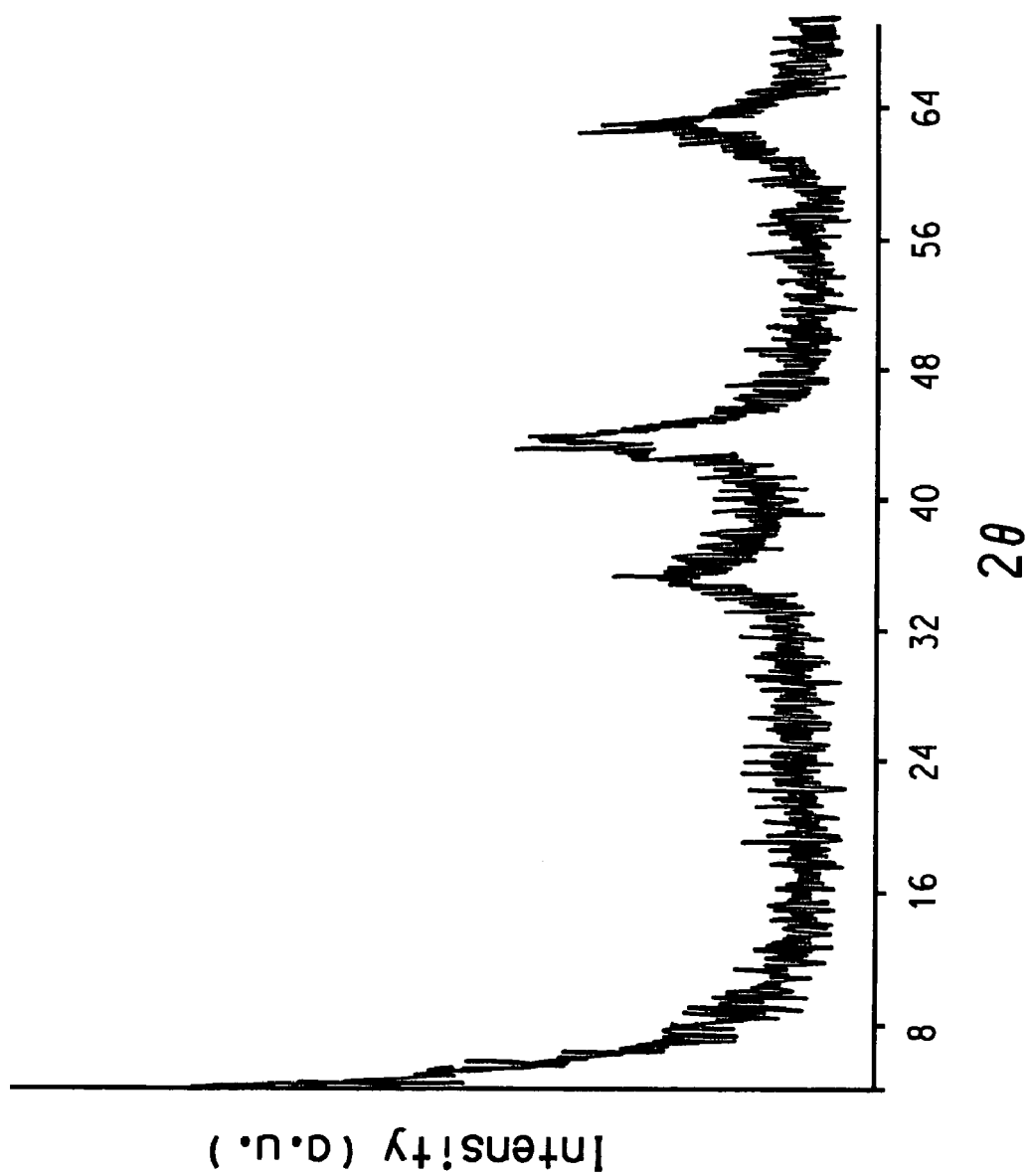
FIG. 2 is a powder X-ray diffraction pattern of the same hydrotaclite after thermal decomposition.

After the hydrotalcite is thermally decomposed, the intensities of the first three major peaks will be diminished, as shown in FIG. 2 (also taken from Das, et al.).

In another embodiment, the invention involves the same lactone reaction wherein the catalyst is a composite catalyst that is made by a process comprising:

(f) contacting (i) the product produced in step (e) with (ii) a solution comprising a solvent and a compound of at least one element selected from the group consisting of lithium, sodium, potassium, rubidium, cesium, magnesium, calcium, strontium and barium;

(g) drying the product of step (f) to remove at least a portion of the solvent;

(h) heating the product of step (g) at a temperature in the range of 350° C. to 550° C. to produce a catalyst precursor; and (i) flushing at a preselected flow rate an oxygen-containing gas over said catalyst precursor either during step (h), or after step (h) while the temperature is still in the range of 350° C. to 550° C. to produce the composite catalyst in which the at least one element is present in said composite catalyst in an amount from about 0.1% to about 40% by weight of the combined weight of the product produced in step (e) and the element.

The inclusion of an appropriate Group I and/or Group II element into the thermally decomposed hydrotalcite may cause a shift in the relative number of acid and base sites, which could, in turn, influence catalytic activity.

Aqueous or non-aqueous solutions of organic compounds such as the carboxylates, such as acetate, propionate, butyrate, and 2-ethylhexanoate of a catalytic element selected from the group consisting of lithium, sodium, potassium, rubidium, cesium, magnesium, calcium, strontium and barium may be used. Organic compounds containing acetates are preferred. Other organic anions such as acetylacetonates can be used. The amount of organic compound should be chosen to provide to the final composite catalyst from 0.1 wt % to 40 wt % of the element relative to the combined weight of the product produced in step (d) plus the element (as opposed to the compound of which the element is a part). The resulting material is allowed to dry, preferably in a nitrogen environment for an extended time. The purpose of the drying is to remove at least a portion of the solvent in which the organic compound is dissolved.

Organic compounds such as the alkoxides can also be used. Organic alkoxides of an element selected from the group consisting of lithium, sodium, potassium, rubidium, cesium, magnesium, calcium, strontium, and barium can contain from one to 20 carbon atoms and preferably 1 to 5 carbon atoms in the alkoxy group. The organic alkoxide should be soluble in the solvent. Most alkoxides can be dissolved in non-aqueous solutions such as ethanol, propanol, or isopropyl alcohol. Subsequent methods for introducing the element and drying are the same.

The dried material is then heated (for example in an alumina boat placed in a tube furnace) at an ambient temperature of 300° C. to 550° C. (The temperature of the catalyst material may be somewhat higher because of exothermic reactions taking place on the material.) Either during the heating or subsequent to it, but at the same temperature, the material is flushed with an oxygen-containing gas (e.g. air), which is believed to burn off organic residues formed during the heating step. In a tube furnace, an airflow rate of at least 110 cc/min in a 3 cm diameter tube furnace, which corresponds to a linear velocity of 15.6 cm/min was found to be acceptable. In a tube furnace, the material can be heated at a rate of 5° C./min to 120° C., and can be exposed to this temperature for 4 hours. It can be heated subsequently at a rate of 5° C./min to approximately 450° C. and held at this temperature for 16 hours. Other equipment can be used to perform the heating step. Such equipment includes fluidized bed and rotary calcination equipment.

Heating can be accomplished in air or in a combination of an inert gas such as nitrogen, argon, or krypton for parts of the cycle, followed by air. An initial drying step at 120° C. in nitrogen, another inert gas, or air is preferred for a period of 30 minutes to 24 hours. Following this drying step, the catalyst can be heated in air or nitrogen to a temperature of 300° C. to 550° C. Heating times can range from 30 minutes to 48 hours. The final heating step preferably is performed in air for at least 30 minutes.

In some cases, reaction conditions may result in a decrease of catalyst efficiency. In these situations it may be useful to periodically reactivate the catalyst. For example, contacting the present catalysts, when activity drops below an acceptable level, with oxygen at elevated temperatures may have the effect of reactivating the catalyst. Contact temperatures with oxygen may range from about 225° C. to about 500° C., with temperatures of about 250° C. to about 425° C. being preferred.

Thermal and hydrothermal stability are required for the catalyst to withstand one or repeated regeneration cycles without permanently degrading catalyst performance.

Selectivities and yields of product may be influenced by the total contact time with the catalyst. As stated previously, yields and selectivities may be increased by adjusting gas and liquid flow rates.

Separation and/or purification of the desired products, including MBL or MeMBL, from unreacted starting lactone and/or reaction byproducts may be performed by processes known in the art. A particularly suitable method to recover the desired product is to polymerize MBL in GBL solution, or MeMBL in GVL solution, using standard free-radical polymerization, isolate the polymer by precipitation, and then thermally depolymerize back to MBL or MeMBL, as the case may be, by heating under vacuum. Finally, MBL can be separated from GBL by melt crystallization. Another effective method is liquid-liquid extraction.

Non-limiting reactors suitable for the process of the instant invention include a tubular reactor, fluidized bed reactor, fixed bed reactor, and transport bed reactor. The process can be run in either batch or continuous mode as described, for example, in H. Scott Fogler, *Elements of Chemical Reaction Engineering*, $2^{nd}$ Edition, Prentice-Hall Inc, CA, 1992.

The reaction can be carried out by passing solutions of the formaldehyde and lactone over the catalyst at elevated temperatures.

EXAMPLES

Catalyst 1:

20 wt % Ba on decomposed $(M^{2+}_{1-x}M^{3+}_{x}(OH)_2)$ $(A^{n-}_{x/n}) \cdot yH_2O$, where $M^{2+}$=Zn and Mg, $M^{3+}$=Al, x=0.382      Catalyst 1

Barium acetate (Aldrich, Milwaukee Wis.) was dissolved in approximately 40 ml water and was allowed to contact approximately 10 g of ⅛" Hydrotalcite Extrudates (Sud-Chemie). The hydrotalcite has an atomic ratio Zn 0.16 Mg 0.46 Al 0.382. The resulting material was allowed to dry at room temperature and was loaded into a 1" diameter fritted quartz tube. The material was heated in a vertical tube furnace according to the following schedule: (All process steps were performed in at least 100 standard cubic centimeters per minute of flowing air) (i) heat to 120° C., and hold at 120° C.; heat at a rate of 5° C./minute to 300° C., and hold for five hours at 300° C.; cool to room temperature.

Catalyst 2:

Decomposed $(M^{2+}_{1-x}M^{3+}_{x}(OH)_2)(A^{n-}_{x/n}) \cdot yH_2O$, where $M^{2+}$=Mg, $M^{3+}$Al, x=0.25

In a one liter round bottom flask, 51.28 g of magnesium nitrate hexahydate, $Mg(NO_3)_2 \cdot 6H_2O$ (EM Sciences) and 25.01 g of aluminum nitrate (EM Sciences) were dissolved in approximately 500 ml of water. The solution was heated to 60° C. to 70° C. Approximately 140 ml of 30 wt % ammonium hydroxide was slowly added to the stirred solution over a period of about 1 hour. After stirring for another 30 minutes at 60° C., the mixture was allowed to cool to room temperature.

The material, which was a cloudy precipitate, was dried overnight at room temperature, in flowing nitrogen, before heating.

The dried material was loaded into an alumina boat and heated in a horizontal tube furnace. The airflow rate corresponded to a linear velocity of 15.6 cm/min. The material was heated at a rate of 5° C./min to 120° C.; this temperature (120° C.) was maintained for four hours. It was subsequently heated at a rate of 5° C./min to approximately 450° C. and then allowed to cool to room temperature in flowing air.

Catalyst 3:

Decomposed $(M^{2+}_{1-x}M^{3+}_x(OH)_2)(A^{n-}_{x/n}) \cdot yH_2O$, where $M^{2+}$=Mg, $M^{3+}$Al, x=0.25

A similar procedure as described for catalyst 2 was used; however, a more dilute aqueous combined solution of magnesium and aluminum nitrate was employed.

10.26 grams of $Mg(NO_3)_2 \cdot 6H_2O$ was dissolved in 400 ml of water in a 1 liter round bottom flask. To this solution, 5 g of aluminum nitrate dissolved in 10 ml of water was added. The solution was stirred, and the temperature was raised to 60° C. to 70° C. About 50 milliters of 30 wt % $NH_4OH$ was added to this solution over a period of 1 hour. The solution was stirred for another 30 minutes and then allowed to cool over a two hour time period (while stirring) to room temperature. The precipitate was dried under nitrogen for about 12 hours.

The dried material was loaded into an alumina boat and heated in a tube furnace. The airflow rate corresponded to a linear velocity of 15.6 cm/min. The material was heated at a rate of 5° C./min to 120° C.; this temperature (120° C.) was maintained for four hours. It was subsequently heated at a rate of 5° C./min to approximately 450° C. and then allowed to cool to room temperature in flowing air.

Example of Vapor Phase Reaction

Solutions containing gamma-valerolactone in formalin (37% aqueous formaldehyde), at various feed ratios, were fed to a vaporizer (held at 200° C.) followed by the introduction of nitrogen, to carry the vapor through a ¼ inch tubular reactor containing a catalyst heated to the appropriate reaction temperature. In the following examples, nitrogen flow rate was 24 cc/min., liquid feed rate was 1 ml/hr, formaldehyde to GVL molar ratio was 4:1 and the catalyst volume was 2 cc. The TOS (hours) was typically 0.5 to 5 hours. The reactor effluent was condensed in a cold trap and analyzed off-line by GC-MS using an internal standard. Conversion is based on the weight percent of GVL converted, and selectivity was based on the weight fraction of each compound relative to the amount of GVL converted.

TABLE 1

Reaction Data

| Catalyst | Feed cc/hr | TOS (hr) | % GVL Conv | % MeMBL Sel |
|---|---|---|---|---|
| Catalyst 1 | 1 | 0.5 | 8.05 | 100.00 |
| Catalyst 1 | 1 | 1 | 6.29 | 100.00 |
| Catalyst 1 | 1 | 1.5 | 5.41 | 100.00 |
| Catalyst 1 | 1 | 2 | 4.93 | 97.15 |
| Catalyst 2 | 1.12 | 0.5 | 5.79 | 100.00 |
| Catalyst 2 | 1.12 | 1 | 4.35 | 100.00 |
| Catalyst 2 | 1.12 | 1.5 | 3.68 | 95.03 |
| Catalyst 2 | 1.12 | 2 | 3.17 | 93.75 |
| Catalyst 2 | 1.12 | 3 | 2.65 | 92.36 |
| Catalyst 2 | 1.12 | 4.5 | 2.16 | 90.33 |
| Catalyst 3 | 1.12 | 0.75 | 9.04 | 94.92 |
| Catalyst 3 | 1.12 | 1.25 | 8.65 | 94.23 |
| Catalyst 3 | 1.12 | 1.5 | 8.02 | 93.93 |
| Catalyst 3 | 1.12 | 2 | 6.91 | 93.95 |
| Catalyst 3 | 1.12 | 3 | 6.12 | 92.99 |

The data in Table 1 show that reactions done in accordance with the process of the present invention yield the desired products with modest conversion and high selectivity.

What is claimed is:

1. A process for preparing a reaction product comprising an alpha-methylene lactone of the Formula II, said process comprising reacting a lactone of the Formula I with formaldehyde,

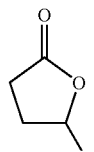

I

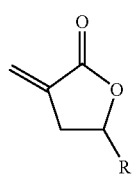

II wherein R is selected from the group consisting of hydrogen, methyl, ethyl, and straight or branched $C_3$-$C_5$ alkyl; at a temperature in the range of from about 150° C. to about 450° C. in the presence of a catalyst derived from a hydrotalcite of the formula:

$(M^{2+}_{1-x} M^{3+}_x(OH)_2)(A^{n-}_{x/n}) \cdot yH2O$ wherein $M^{2+}$ is Mg, or a combination of Mg and at least one of Zn, Ni, Co, Fe, and Cu; and $M^{3+}$ is Al, or a combination of Al and at least one of Fe and Cr; x is 0.66 to 0.1 and A is $CO_3$ with n=2, or OH with n=1, by a process comprising heating the hydrotalcite for a time and a temperature sufficient to cause a diminution in the hydrotalcite powder X-ray diffraction pattern peak intensities between 2θ angles of 10 degrees and 70 degrees using $CuK_\alpha$ radiation.

2. The process of claim 1, wherein the catalyst is made by a process comprising:
   (a) combining at least one aluminum salt and at least one magnesium salt, and optionally at least one salt of an element selected from the group consisting of Zn, Ni, Co, Fe, Cu and Cr, to form an aqueous solution;
   (b) optionally heating the aqueous solution to 60° C.;
   (c) adjusting the pH of the material produced in step (a) or step (b) with base or sodium carbonate to precipitate any hydroxides, carbonates or hydroxide carbonates that are formed;
   (d) drying the material produced in step (c) to produce a hydrotalcite; and
   (e) heating the hydrotalcite produced in step (d) for a time and a temperature sufficient to cause a diminution in the hydrotalcite powder X-ray diffraction pattern peak intensities between 2θ angles of 10 degrees and 70 degrees using $CuK_\alpha$ radiation.

3. The process of claim 2, wherein the catalyst is made by a process further comprising the steps of:
   (f) contacting (i) the product produced in step (e) with (ii) a solution comprising a solvent and a compound of at least one element selected from the group consisting of lithium, sodium, potassium, rubidium, cesium, magnesium, calcium, strontium and barium;
   (g) drying the product of step (f) to remove at least a portion of the solvent;
   (h) heating the product of step (g) at a temperature in the range of 350° C. to 550° C. to produce a catalyst precursor; and (i) flushing at a preselected flow rate an oxygen-containing gas over said catalyst precursor either during step (h), or after step (h) while the temperature is still in the range of 350° C. to 550° C. to produce the composite catalyst in which the at least one element is present in said composite catalyst in an amount from about 0.1% to about 40% by weight of the combined weight of the product produced in step (e) and the element.

* * * * *